United States Patent [19]

Simmons

[11] Patent Number: 4,707,496

[45] Date of Patent: Nov. 17, 1987

[54] INSECT REPELLENT SOAP COMPOSITION

[75] Inventor: Thomas E. Simmons, Victoria, Australia

[73] Assignee: Simmons Nominees Pty. Ltd., Doncaster East, Australia

[21] Appl. No.: 719,707

[22] Filed: Apr. 4, 1985

[30] Foreign Application Priority Data

Jul. 19, 1984 [AU] Australia ............................... PG6106

[51] Int. Cl.$^4$ ..................... A01N 25/00; A01N 31/00; A01N 37/18; A01N 53/00
[52] U.S. Cl. .................................. 514/531; 252/107; 424/DIG. 10; 514/617; 514/738; 514/784; 514/918; 514/919
[58] Field of Search ............... 424/DIG. 10; 252/107; 514/531, 617, 918, 919, 784, 738

[56] References Cited

U.S. PATENT DOCUMENTS

| | | | |
|---|---|---|---|
| 308,172 | 11/1884 | Zacherl | 252/107 |
| 1,451,670 | 4/1923 | MacPherson et al. | 252/107 |
| 2,465,470 | 3/1949 | Omohundro et al. | 424/DIG. 10 |
| 3,043,778 | 7/1962 | Kelly | 252/107 |
| 3,172,803 | 3/1965 | Birum | 252/107 |
| 3,179,596 | 4/1965 | Farrar et al. | 252/107 |
| 3,634,264 | 1/1972 | Pence | 252/107 |
| 4,064,268 | 12/1977 | Adolphi et al. | 424/DIG. 10 |
| 4,178,384 | 12/1979 | Ensing | 424/DIG. 10 |
| 4,193,986 | 3/1980 | Cox | 252/107 |

FOREIGN PATENT DOCUMENTS

| | | |
|---|---|---|
| 605317 | 7/1948 | United Kingdom . |
| 1014243 | 12/1965 | United Kingdom . |
| 1197817 | 7/1970 | United Kingdom ................ 252/107 |
| 1489341 | 10/1977 | United Kingdom . |

OTHER PUBLICATIONS

Bennett, The Chemical Formulary (1951), p. 532.

Primary Examiner—Allen J. Robinson
Attorney, Agent, or Firm—Michael N. Meller

[57] ABSTRACT

The invention relates to a topical insect repellent soap composition and to a method of protection using such a composition. Generally, the insect repellent soap composition comprises:

(1) from 63.0 to 99.5% by wt of a soap mixture containing from 4.1 to 7% by wt of a soap of caprylic acid, from 3.8 to 7% of a soap of capric acid, from 32.1 to 45% of a soap of lauric acid, from 12 to 17.5% by wt of a soap of myristic acid, from 5.0 to 10% by wt of a soap of palmitic acid, from 1.6 to 3% by wt of a soap of stearic acid, from 3.5 to 5% by wt of a soap of oleic acid and from 0.9 to 5% by wt of a soap of linoleic acid;

(2) from 0.1 to 2% by wt of $C_8$–$C_{18}$ straight chain fatty acids;

(3) from 0.2 to 30% by wt of a repellent chemical;

(4) from 0.2 to 5% by wt of an effective residual insecticide.

15 Claims, No Drawings

INSECT REPELLENT SOAP COMPOSITION

This invention relates to a topical insect repellent soap composition and to a method of protection using such a composition.

The composition can be used in the form of a toilet soap bar and contains specific ingredients for repelling and killing insects, in particular flies and mosquitoes, thus giving protection from their bites.

BACKGROUND TO INVENTION

Product forms of topical insect repellents are quite diverse and include simple liquids, lotions, creams, gels, sticks, aerosol sprays and foams and single-use impregnated towelettes. It is an object of the present invention to provide a toilet soap type product which when used according to directions, leaves a film on the skin that gives protection against biting flies and mosquitoes and which has the following important properties:

(a) is a mild non-irritating toilet soap having a composition that is compatible when combined with optimum high concentrations of repellent chemicals;

(b) has a sufficiently high concentration of safe proven repellent chemicals to provide maximum intrinsic repellency as well as prolonged repellency; and (c) is a combination of the repellent chemical with an effective residual insecticide.

This invention relates to an insect repellent soap composition, which comprises:

(1) from 63.0 to 99.5 (preferably 72 to 89.7)% by wt of a soap mixture containing from 4.1 to 7% by wt of a soap of caprylic acid, from 3.8 to 7% of a soap of capric acid, from 32.1 to 45% of a soap of lauric acid, from 12 to 17.5% by wt of a soap of myristic acid, from 5.0 to 10% by wt of a soap of palmitic acid, from 1.6 to 3% by wt of a soap of stearic acid, from 3.5 to 5% by wt of a soap of oleic acid and from 0.9 to 5% by wt of a soap of linoleic acid;

(2) from 0.1 to 2 (preferably 0.1 to 1)% by wt of $C_8$–$C_{18}$ straight chain fatty acids;

(3) from 0.2 to 30 (preferably 10 to 25)% by wt of a repellent chemical, preferably N,N-diethyl-metatoluamide;

(4) from 0.2 to 5 (preferably 0.2 to 2)% by wt of an effective residual insecticide, preferably a synthetic pyrethroid, for example, 3-phenoxybenzyl($\pm$), cis trans-2,2-dimethyl-3-(2,2-dichlorvinyl)cyclopropane-1-carboxylate, known as PERMETHRIN 25/75.

This invention also provides a method for protection of animals, in particular humans, against biting insects, in particular flies and mosquitoes, which comprises applying to the skin of such animal an effective amount of a composition according to the invention.

The composition according to the invention gives considerable protection against insects such as flies and biting (female) mosquitoes. It is believed that the composition according to the invention affects mosquitoes in two ways. Firstly, it uses topical repellents which interfere with the sensors of the female mosquito deflecting it from its attack path. Secondly, if by chance some mosquitoes avoid deflection by the repellent chemical, they are killed on contact with a residual film of insecticide left on the skin.

The soap compositions according to the invention contain very high percentages of active ingredients. These ingredients are incompatible with ordinary soap bases. It is not possible to incorporate these ingredients into such soaps even by boiling, since boiling would destroy the ingredients. Hence, active materials which are compatible with vegetable oil-based soaps, even at room temperature, are selected.

Other optional ingredients are non-physiologically harmful perfumes and colorants.

Soap compositions according to the present invention are not limited or restricted to the use of N,N-diethyl-metatoluamide as the repellent but may include one or more of the following repellent chemicals:

(i) N,N-diethyl-2-ethoxybenzamide
(ii) N,N-dipropyl-2-benzyloxyacetamide
(iii) 1-butyl-4-methylcarbostyril
(iv) N,N-dipropyl-2-ethoxybenzamide
(v) 2-butyl-2-ethyl-1,3-propanediol
(vi) 1,3-bis-butoxymethyl-2-imidazolidone
(vii) hexachlorophenol
(viii) 1,3-propanediol monobenzoate
(ix) diisobutyl malate
(x) ethyl hexanediol
(xi) dibutyl phthalate
(xii) butyl-3-4-dihydro-2,2dimethyl-4-oxo-2h-1,3-oxazine
(xiii) 1,5a,6,9,9a,9b-hexahydro-4a-(4H)-dibenzofuran-carboxaldehyde
(xiv) di-n-propyl-2,5-pyridinedicarboxylate
(xv) 3-acetyl-2-(2-6-dimethyl-5-heptenyl)-oxazolidine The following Example illustrates one composition according to the invention:

EXAMPLE 1

The following ingredients were mixed at room temperature and then made up into the form of soap bars:

|  | % by wt. |
| --- | --- |
| Soap of caprylic acid | 5.6 |
| Soap of capric acid | 5.2 |
| Soap of lauric acid | 44.0 |
| Soap of myristic acid | 16.0 |
| Soap of palmitic acid | 7.0 |
| Soap of stearic acid | 2.2 |
| Soap of oleic acid | 4.3 |
| Soap of linoleic acid | 2.2 |
| N,N—diethyl-meta-toluamide | 12.0 |
| Permethrin 25/75 | 1.0 |
| $C_8$—$C_{18}$ straight chain fatty acids | 0.5 |
|  | 100.0 |

EXAMPLE 2

The following ingredients were mixed at room temperature and then made up into the form of soap bars:

|  |  |
| --- | --- |
| Soap of caprylic acid | 4.76 |
| Soap of capric acid | 4.4 |
| Soap of lauric acid | 37.35 |
| Soap of myristic acid | 13.9 |
| Soap of palmitic acid | 5.86 |
| Soap of stearic acid | 1.83 |
| Soap of oleic acid | 4.03 |
| Soap of linoleic acid | 1.1 |
| N,N—diethyl-meta-toluamide | 11.5 |
| Permethrin 25/75 | 0.5 |
| $C_8$—$C_{18}$ straight chain fatty acids | 0.6 |
| Repellent chemical (xiii) above | 7.0 |
| Repellent chemical (xiv) above | 7.17 |
|  | 100.0 |

The compositions according to the Examples are effective against mosquitoes. A soap bar according to the invention was used as follows:

Water was sprinkled lightly onto the forearms of a human volunteer. The soap bar was rubbed gently on the wet skin to form a lather. This was allowed to dry on the skin to form a repellent film. Repellent activity was observed for up to 12 hours.

I claim:

1. An insect repellent soap composition, which comprises:
    (1) from 63.0 to 89.7% by wt of a water soluble soap mixture containing from 4.1 to 7% by wt of a soap of caprylic acid, from 3.8 to 7% of a soap capric acid, from 32.1 to 45% of a soap of lauric acid, from 12 to 17.5% by wt of a soap of myristic acid, from 5.0 to 10% by wt of a soap of palmitic acid, from 1.6 to 3% by wt of a soap of stearic acid, from 3.5 to 5% by wt of a soap of oleic acid and from 0.9 to 5% by wt of a soap of linoleic acid;
    (2) from 0.1 to 2% by wt of $C_8$–$C_{18}$ straight chain fatty acids;
    (3) from 10 to 30% by wt of an insect repellent chemical;
    (4) from 0.2 to 5% by wt of 3-phenoxybenzyl($\pm$), cis trans-2,2-dimethyl-3-(2,2-dichlorovinyl)cyclopropane-1-carboxylate.

2. A composition as claimed in claim 1, wherein ingredient (1) is present in an amount from 72 to 89.7% by wt.

3. A composition as claimed in claim 1, wherein ingredient (2) is present in an amount from 0.1 to 1% by wt.

4. A composition as claimed in claim 1, wherein ingredient (3) is present in an amount from 10 to 25% by wt.

5. A composition as claimed in claim 1, wherein ingredient (4) is present in an amount from 0.2 to 2% by wt.

6. A composition as claimed in claim 1, wherein the repellent chemical of ingredient (3) is N,N-diethyl-metatoluamide.

7. A composition as in claim 4, wherein the repellent chemical of ingredient (3) is N,N-diethyl-metatoluamide.

8. A composition as claimed in claim 1, wherein the repellent is ethyl hexandiol.

9. A method for protection of animals and humans against biting insects which comprises applying to the skin of such animal or human an insect repellent effective amount of a composition as defined in claim 1.

10. A method for protection of animals and humans against biting insects which comprises applying to the skin of such animal or human an insect repellent effective amount of a composition as defined in claim 2.

11. A method for protection of animals and humans against biting insects which comprises applying to the skin of such animal or human an insect repellent effective amount of a composition as defined in claim 3.

12. A method for protection of animals and humans against biting insects which comprises applying to the skin of such animal or human an insect repellent effective amount of a composition as defined in claim 4.

13. A method for protection of animals and humans against biting insects which comprises applying to the skin of such animal or human an insect repellent effective amount of a composition as defined in claim 5.

14. A method for protection of animals and humans against biting insects which comprises applying to the skin of such animal or human an insect repellent effective amount of a composition as defined in claim 6.

15. A method for protection of animals and humans against biting insects which comprises applying to the skin of such animal or human an insect repellent amount of a composition as defined in claim 8.

* * * * *